United States Patent [19]
Grotendorst et al.

[11] Patent Number: 6,149,916
[45] Date of Patent: *Nov. 21, 2000

[54] METHODS OF ACCELERATING WOUND HEALING OR OF STIMULATING CONNECTIVE TISSUE CELL GROWTH USING CONNECTIVE TISSUE GROWTH FACTOR

[75] Inventors: Gary R. Grotendorst, Lutz, Fla.; Douglass M. Bradham, Jr., Baltimore, Md.

[73] Assignee: University of South Florida, Tampa, Fla.

[ * ] Notice: This patent is subject to a terminal disclaimer.

[21] Appl. No.: 09/097,179

[22] Filed: Jun. 12, 1998

Related U.S. Application Data

[62] Division of application No. 08/712,302, Sep. 11, 1996, Pat. No. 5,783,187, which is a division of application No. 08/386,680, Feb. 10, 1995, Pat. No. 5,585,270, which is a division of application No. 08/167,628, Dec. 14, 1993, Pat. No. 5,408,040, which is a continuation of application No. 07/752,427, Aug. 30, 1991, abandoned.

[51] Int. Cl.⁷ ..................................................... A61K 38/18
[52] U.S. Cl. ......................................... 424/198.1; 530/399
[58] Field of Search ........................ 424/198.1; 530/399, 530/387.9; 435/69.4; 930/120; 514/12

[56] References Cited

U.S. PATENT DOCUMENTS

| | | |
|---|---|---|
| 5,094,941 | 3/1992 | Hart . |
| 5,147,294 | 9/1992 | Smith et al. . |
| 5,149,691 | 9/1992 | Rutherford ................................. 514/12 |
| 5,356,630 | 10/1994 | Laurencin et al. ....................... 424/426 |
| 5,399,361 | 3/1995 | Song et al. .............................. 424/486 |
| 5,408,040 | 4/1995 | Grotendorst et al. .................... 530/399 |
| 5,418,135 | 5/1995 | Pang . |
| 5,770,209 | 6/1998 | Grotendorst et al. ................. 424/198.1 |

OTHER PUBLICATIONS

Shimokado et al., Cell 43:277–286, Nov. 1985.
Campochiaro et al., Exp. Eye Res. 49:217–227, 1989.
Matsuoka et al., Proc. Nat. Acad. Sci. 86:4416–4420, Jun. 1989.
Ryseck, R.P. et al., Cell Growth and Differentiation 2:225–233, May 1991.
Bradham et al., "Connective Tissue Growth Factor: a Cysteine–rich Mitogen Secreted by Human Vascular Endothelial cells is Related to the SRC–induced Immediate Early Gene Product CEF–10," *J. Cell Biology*, 114(6):1285–1294 (1991).
Oemar et al., "Connective Tissue Growth Factor, Friend or Foe?" *Arteriosclerosis, Thrombosis, and Vascular Biology*, 17(8):1483–1489 (1997).

*Primary Examiner*—Lorraine Spector
*Attorney, Agent, or Firm*—Gray Cary Ware & Freidenrich LLP; Lisa A. Haile

[57] ABSTRACT

Connective Tissue Growth Factor (CTGF), means for producing CTGF, as well as diagnostic and therapeutic methods for using CTGF.

3 Claims, No Drawings

METHODS OF ACCELERATING WOUND HEALING OR OF STIMULATING CONNECTIVE TISSUE CELL GROWTH USING CONNECTIVE TISSUE GROWTH FACTOR

This is a divisional of U.S. application Ser. No. 08/712,302, filed Sep. 11, 1996, now U.S. Pat. No. 5,783,187, which is a Divisional of Ser. No. 08/386,680, filed Feb. 10, 1995—now U.S. Pat. No. 5,585,270—which is a Divisional of Ser. No. 08/167,628, filed Dec. 14, 1993—now U.S. Pat. No. 5,408,040—which is a Continuation of Ser. No. 07/752,427, filed Aug. 30, 1991, now abandoned.

BACKGROUND OF THE INVENTION

1. Field of the Invention

This invention relates generally to the field of growth factors and specifically to Connective Tissue Growth Factor (CTGF) and the gene encoding this factor.

2. Related Art

Growth factors are a class of secreted polypeptides that stimulate target cells to proliferate, differentiate and organize in developing tissues. The action of growth factors is dependent an their binding to specific receptors which stimulates a signalling event within the cell. Examples of some well-studied growth factors include platelet-derived growth factor (PDGF), insulin-like growth factor (IGF-I), transforming growth factor beta (TGF-$\beta$), transforming growth factor alpha (TGF-$\alpha$), epidermal growth factor (EGF), and fibroblast growth factor (FGF).

PDGF is a cationic, heat-stable protein found in the alpha-granules of circulating platelets and is known to be a mitogen and a chemotactic agent for connective tissue cells such as fibroblasts and smooth muscle cells. Because of the activities of this molecule, PDGF is believed to be a major factor involved in the normal healing of wounds and pathologically contributing to such diseases as atherosclerosis and fibrotic diseases. PDGF is a dimeric molecule consisting of an A chain and a B chain. The chains form heterodimers or homodimers and all combinations isolated to date are biologically active.

Studies on the role of various growth factors in tissue regeneration and repair have led to the discovery of PDGF-like proteins. These proteins share both immunological and biological activities with PDGF and can be blocked with antibodies specific to PDGF.

These new growth factors may play a significant role in the normal development, growth, and repair of human tissue. Therapeutic agents derived from these molecules may be useful in augmenting normal or impaired growth processes involving connective tissues in certain clinical states, e.g., wound healing. When these growth factors are involved pathologically in diseases, therapeutic developments from these proteins may be used to control or ameliorate uncontrolled tissue growth.

The isolation of these factors and the genes encoding them is important in the development of diagnostics and therapeutics for various connective tissue-related disorders. The present invention provides such an invention.

SUMMARY OF THE INVENTION

Various cell types produce and secrete PDGF and PDGF-related molecules. In an attempt to identify the type of PDGF dimers present in the growth media of cultured endothelial cells, a new growth factor was discovered. This previously unknown factor, termed Connective Tissue Growth Factor (CTGF), is related immunologically and biologically to PDGF, however it is the product of a distinct gene.

In a first aspect, the present invention relates to a polypeptide growth factor for connective tissue cells. The polypeptide is mitogenic and is also a chemotactic agent for cells.

In a second aspect, the present invention provides a polynucleotide encoding a connective tissue growth factor characterized as encoding a protein (1) existing as a monomer of approximately 36–38 kD molecular weight, and (2) capable of binding to a PDGF receptor.

In a further aspect, the invention provides a method for accelerating wound healing in a subject by applying to the wound an effective amount of a composition which contains purified CTGF.

In yet another aspect, the invention provides a method of diagnosing pathological states in a subject suspected of having pathology characterized by a cell proliferative disorder which comprises, (1) obtaining a sample suspected of containing CTGF from the subject, (2) determining the level of CTGF in the sample, and (3) comparing the level of CTGF in the sample to the level of CTGF in normal tissues.

A method of ameliorating diseases characterized by a cell proliferative disorder, by treating the site of the disease with an effective amount of a CTGF reactive agent is also provided.

DETAILED DESCRIPTION OF THE INVENTION

The present invention discloses a novel protein growth factor called Connective Tissue Growth Factor (CTGF). This protein may play a significant role in the normal development, growth and repair of human tissue. The discovery of the CTGF protein and cloning of the cDNA encoding this molecule is significant in that it is a previously unknown growth factor having mitogenic and chemotactic activities for connective tissue cells. The biological activity of CTGF is similar to that of PDGF, however, CTGF is the product of a gene unrelated to the A or B chain genes of PDGF. Since CTGF is produced by endothelial and fibroblastic cells, both of which are present at the site of a wound, it is probable that CTGF functions as a growth factor in wound healing. Pathologically, CTGF may be involved in diseases in which there is an overgrowth of connective issue cells, such as cancer, fibrotic diseases and atherosclerosis. The CTGF polypeptide could be useful as a therapeutic in cases in which there is impaired healing of skin wounds or there is a need to augment the normal healing mechanisms. Additionally, antibodies to CTGF polypeptide or fragments could be valuable as diagnostic tools to aid in the detection of diseases in which CTGF is a pathological factor. Therapeutically, antibodies or fragments of the antibody molecule could also be used to neutralize the biological activity of CTGF in diseases where CTGF is inducing the overgrowth of tissue.

The primary biological activity of CTGF polypeptide is its mitogenicity, or ability to stimulate target cells to proliferate. The ultimate result of this mitogenic activity in vivo, is the growth of targeted tissue. CTGF also possesses chemotactic activity, which is the chemically induced movement of cells as a result of interaction with particular molecules. Preferably, the CTGF of this invention is mitogenic and chemotactic for connective tissue cells, however, other cell types may be responsive to CTGF polypeptide as well.

The CTGF polypeptide of the invention is characterized by existing as a monomer of approximately 36–38 kD molecular weight. CTGF is secreted by cells and is active upon interaction with a PDGF receptor of cells. CTGF is antigenically related to PDGF although there is little if any peptide sequence homology. Anti-PDGF antibody has high affinity to the non-reduced forms of the PDGF isomers and the CTGF molecule and ten-fold less affinity to the reduced forms of these peptides, which lack biological activity. This suggests that there are regions of shared tertiary structure between the PDGF isomers and the CTGF molecule, resulting in common antigenic epitopes.

The term "substantially pure" as used herein refers to CTGF which is substantially free of other proteins, lipids, carbohydrates or other materials with which it is naturally associated. The substantially pure polypeptide will yield a single major band on a non-reducing polyacrylamide gel. The purity of the CTGF polypeptide can also be determined by amino-terminal amino acid sequence analysis. CTGF polypeptide includes functional fragments of the polypeptide, so long as the mitogenic and chemotactic activities of CTGF are retained. Smaller peptides containing the biological activity of CTGF are included in the invention. Additionally, more effective CTGF molecules produced, for example, through site directed mutagenesis of the CTGF cDNA are included.

The invention provides polynucleotides encoding the CTGF protein. These polynucleotides include DNA, cDNA and RNA sequences which encode connective tissue growth factor. It is understood that all polynucleotides encoding all or a portion of CTGF are also included herein, so long as they encode a polypeptide with the mitogenic and chemotactic activity of CTGF. Such polynucleotides include both naturally occurring and intentionally manipulated polynucleotides. For example, CTGF polynucleotide may be subjected to site-directed mutagenesis. The polynucleotides of the invention include sequences that are degenerate as a result of the genetic code. There are only 20 natural amino acids, most of which are specified by more than one codon. Therefore as long as the amino acid sequence of CTGF is functionally unchanged, all degenerate nucleotide sequences are included in the invention.

The sequence of the cDNA for CTGF contains an open reading frame of 1047 nucleotides with an initiation site at position 130 and a TGA termination site at position 1177 and encodes a peptide of 349 amino acids. There is only a 40% sequence homology between the CTGF cDNA and the cDNA for both the A and B chains of PDGF.

The CTGF open reading frame encodes a polypeptide which contains 39 cysteine residues, indicating a protein with multiple intramolecular disulfide bonds. The amino terminus of the peptide contains a hydrophobic signal sequence indicative of a secreted protein and there are two N-linked glycosylation sites at asparagine residues 28 and 225 in the amino acid sequence. There is a 45% overall sequence homology between the CTGF polypeptide and the polypeptide encoded by the CEF-10 mRNA transcript (Simmons, et al., *Proc. Natl. Acad. Sci.* USA 86:1178, 1989); the homology reaches 52% when a putative alternative splicing region is deleted.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences and 2) antibody screening of expression libraries to detect shared structural features.

Screening procedures which rely on nucleic acid hybridization make it possible to isolate any gene sequence from any organism, provided the appropriate probe is available. For example, oligonucleotide probes, which correspond to a part of the sequence encoding the protein in question, can be synthesized chemically. This requires that short, oligopeptide, stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research,* 9:879, 1981).

A cDNA expression library, such as lambda gt11, can be screened indirectly for CTGF peptides having at least one epitope, using antibodies specific for CTGF or antibodies to PDGF which cross react with CTGF. Such antibodies can be either polyclonally or monoclonally derived and used to detect expression product indicative of the presence of CTGF cDNA.

DNA sequences encoding CTGF can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used.

DNA sequences encoding CTGF can be expressed in vivo in either prokaryotes or eukaryotes. Methods of expressing DNA sequences having eukaryotic coding sequences in prokaryotes are well known in the art. Host include microbial, yeast and mammalian organisms.

Biologically functional viral and plasmid DNA vectors capable of expression and replication in a host are known in the art. Such vectors are used to incorporate DNA sequences of the invention. In general, expression vectors containing promotor sequences which facilitate the efficient transcription of the inserted eukaryotic genetic sequence are used in connection with the host The expression vector typically contains an origin of replication, a promoter, and a terminator, as well as specific genes which are capable of providing phenotypic selection of the transformed cells.

In addition to expression vectors known in the art such as bacterial, yeast and mammalian expression systems, baculovirus vectors may also be used. One advantage to expression of foreign genes in this invertebrate virus expression vector is that it is capable of expression of high levels of recombinant proteins, which are antigenically and functionally similar to their natural counterparts. Baculovirus vectors and the appropriate insect host cells used in conjunction with the vectors will be known to those skilled in the art. The isolation and purification of host cell expressed polypeptides of the invention may be by any conventional means such as, for example, preparative chromatographic separations and immunological separations such as those involving the use of monoclonal or polygonal antibody.

Transformation of the host cell with the recombinant DNA may be carried out by conventional techniques well known to those skilled in the art. Where the host is prokaryotic, such as *E. coli*, competent cells which are capable of DNA uptake can be prepared from cells harvested after exponential growth and subsequently treated by the $CaCl_2$ method using procedures well known in the art. Alternatively, $MgCl_2$ or RbCl could be used.

Where the host used is a eukaryote, various methods of DNA transfer can be used. These include transfection of DNA by calcium phosphate-precipitates, conventional mechanical procedures such as microinjection, insertion of a plasmid encased in liposomes, or the use of virus vectors.

Eukaryotic host cells may also include yeast. For example, DNA can be expressed in yeast by inserting the DNA into appropriate expression vectors and introducing the product into the host cells. Various shuttle vectors for the expression of foreign genes in yeast have been reported (Heinemann, J. et al., *Nature,* 340:205, 1989; Rose, M. et al., *Gene,* 60:237, 1987).

The invention provides antibodies which are specifically reactive with CTGF polypeptide or fragments thereof. Although this polypeptide is cross reactive with antibodies to PDGF, not all antibodies to CTGF will also be reactive with PDGF. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., Nature, 256:495, 1975; *Current Protocols in Molecular Biology,* Ausubel, et al., ed., 1989). Monoclonal antibodies specific for CTGF can be selected, for example, by screening for hybridoma culture supematants which react with CTGF, but do not react with PDGF.

The invention provides a method for accelerating wound healing in a subject, e.g., human, by applying to the wound an effective amount of a composition which contains purified CTGF. PDGF and PDGF-related molecules, such as CTGF, are involved in normal healing of skin wounds. The CTGF polypeptide of this invention is valuable as a therapeutic in cases in which there is impaired healing of skin wounds or there is a need to augment the normal healing mechanisms, e.g., burns. One important advantage to using CTGF protein to accelerate wound healing is attributable to the molecule's high percentage of cysteine residues. CTGF, or functional fragments thereof, is more stable and less susceptible to protease degradaton than PDGF and other growth factors known to be involved in wound healing.

CTGF is produced by endothelial cells and fibroblastic cells, both of which are present at the site of a skin wound. Therefore, agents which stimulate the production of CTGF can be added to a composition which is used to accelerate wound healing. Preferably, the agent of this invention is transforming growth factor beta. The composition of the invention aids in healing the wound, in part, by promoting the growth of connective tissue. The composition is prepared by combining, in a pharmaceutically acceptable carrier substance, e.g., inert gels or liquids, the purified CTGF and TGF-β.

The term "cell proliferative disorder" refers to pathological states characterized by the continual multiplication of cells resulting in an overgrowth of a cell population within a tissue. The cell populations are not necessarily transformed, tumorigenic or malignant cells, but can include normal cells as well. For example, CTGF may be involved pathologically by inducing a proliferative lesion in the intimal layer of an arterial wall, resulting in atherosclerosis. Instead of trying to reduce risk factors for the disease, e.g., lowering blood pressure or reducing elevated cholesterol levels in a subject, CTGF inhibitors or antagonists of the invention would be useful in interfering with the in vivo activity of CTGF associated with atherosclerosis. CTGF antagonists are useful in treating other disorders associated with overgrowth of connective tissues, such as various fibrotic diseases, including scleroderma, arthritis, alcoholic liver cirrhosis, keloid, hypertropic scar.

The present invention provides a method to detect the presence of elevated levels of CTGF to be used diagnostically to determine the presence of pathologies characterized by a cell proliferative disorder. Far example, a sample suspected of containing CTGF is obtained from a subject, the level of CTGF determined and this level is compared with the level of CTGF in normal tissue. The level of CTGF can be determined by immunoassays using anti-CTGF antibodies, for example. Other variations of such assays which are well known to those skilled in the art, such as radioimmunoassay (RIA), ELISA and immunofluorescence can also be used to determine CTGF levels in a sample. Alternatively, nucleic acid probes can be used to detect and quantitate CTGF mRNA for the same purpose.

The invention also discloses a method for ameliorating diseases characterized by a cell proliferative disorder by treating the site of the disease with an effective amount of a CTGF reactive agent. The term "ameliorate" denotes a lessening of the detrimental effect of the disease-inducing response in the patient receiving therapy. Where the disease is due to an overgrowth of cells, an antagonist of CTGF polypeptide is effective in decreasing the amount of growth factor that can bind to a CTGF specific receptor on a cell. Such an antagonist may be a CTGF specific antibody or functional fragments thereof (e.g., Fab, F(ab')$_2$). The treatment requires contacting the site of the disease with the antagonist. Where the cell proliferative disorder is due to a diminished amount of growth of cells, a CTGF reactive agent which is stimulatory is contacted with the site of the disease. For example, TGF-β is one such reactive agent. Other agents will be known to those skilled in the art.

When a cell proliferative disorder is associated with the expression of CTGF, a therapeutic approach which directly interferes with the translation of CTGF messages into protein is possible. For example, antisense nucleic acid or ribozymes could be used to bind to the CTGF mRNA or to cleave it. Artisense RNA or DNA molecules bind specifically with a targeted gene's RNA message, interrupting the expression of that gene's protein product The antisense binds to the messenger RNA forming a double stranded molecule which cannot be translated by the cell. Antisense oligonucleotides of about 15–25 nucleotides are preferred since they are easily synthesized and have an inhibitory effect just like antisense RNA molecules. In addition, chemically reactive groups, such as iron-linked ethylenediaminetetraacetic acid (EDTA-Fe) can be attached to an antisense oligonucleotide, causing cleavage of the RNA at the site of hybridization. These and other uses of antisense methods to inhibit the in vitro translation of genes are well known in the art (Marcus-Sakura, *Anal, Biochem.,* 172:289, 1988).

The following examples are intended to illustrate but not limit the invention. While they are typical of those that might be used, other procedures known to those skilled in the art may alternatively be used.

EXAMPLE 1

Identification and Partial Purification of Mitogen From HUVE Cells PDGF-Immunorelated Cells Human umbilical vein endothelial (HUVE) cells were isolated from fresh human umbilical cords by collagenase perfusion (Jaffe, et al., *Human Pathol.,* 18:234, 1987) and maintained in medium 199 with 20% FCS, 0.68 mM L-glutamine, 20 μg/ml Gentamicin, 90 μg/ml porcine heparin (Sigma, St Louis, Mo.), and 50 μg/ml Endothelial Cell Growth Supplement (Sigma). Cells used for media collection were third passage cells. Cells were identified as endothelial cells by their non-overlapping cobblestone morphology and by positive staining for Factor-VIII related antigen. NRK cells were obtained from American Type Culture, NIH/3T3 cells were a gift from S. Aaronson (NCl, Bethesda, Md.), and both cell lines were maintained in DMEM, 10% FCS, 20 μg/ml Gentamicin. Fetal bovine aortic smooth muscle cells were obtained from tissue explants as previously described (Grotendorst, et al., *Proc. Natl. Acad. Sci. USA,* 78:3669, 1981) and maintained in DMEM, 10% FCS, 20 μg/ml Gentamicin, and used in assays at second or third passage.

Growth Factors and Antibodies

Human PDGF was purified to homogeneity from platelets as described previously (Grotendorst, *Cell,* 36:279, 1984). Recombinant AA, BB, and AB chain dimeric PDGF molecules were obtained from Creative Biomolecules, (Hopkinton, Mass.). FGF was obtained from Sigma. Purified PDGF or synthetic peptides containing the amino and carboxyl sequences of the mature PDGF A and B chain molecules were used to raise antibodies in goats. Goats were immunized with 20 μg of purified PDGF or 50 μg of synthetic peptide in Freunds complete adjuvant by multiple intradermal injections. Immune sera were collected seven days after the fourth rechallenge (in Freunds incomplete adjuvant) and subsequent rechallenges. The anti-PDGF antibody did not show any cross-reactivity to TGF-β, EGF, or FGF in immunoblot analysis. The anti-peptide antibodies were sequence specific and did not cross-react with other synthetic peptide sequences or with recombinant PDGF peptides which did not contain the specific artgenic sequence. This was determined by Western blot and dot blot analysis.

Antibody Affinity Column

Goat anti-human PDGF IgG (150 mg) was covalently bound to 25 mls of Affi-Gel 10 support (BioRad) according to the manufacturers instructions with a final concentration of 6 mg IgG/ml gel. The column was incubated with agitation at 4° C. for 18 hours with 1 liter of HUVE cell media which had been conditioned for 48 hours. The gel was then poured into a column (5×1.5 cm), washed with four volumes of 0.1 N acetic acid made pH 7.5 with ammonium acetate, and the antibody-bound PDGF immunoreactive proteins eluted with 1 N acetic acid. Peak fractions were determined by biological assays and immunoblotting and the fractions pooled.

Initial studies of the PDGF-related growth factors secreted by HUVE cells were done by removing the serum containing growth media from confluent cultures of cells and replacing it with serum-free media. Aliquots of this media were removed periodically and the proteins immunoblotted using an antibody specific for human platelet PDGF. This antibody does not cross-react with any other known growth factors and is able to detect less than 500 picograms of dimeric PDGF or 10 nanograms of reduced, monomeric A or B chain peptide on immunoblots. HUVE cells were grown to confluence in 6 well plates. The growth media was removed, cells washed with PBS and 1 ml of serum-free media was added to each well. The media was removed after conditioning for the period of time from 6–48 hours, dialyzed against 1 N acetic acid and lyophilized. The samples were then run on 12% PAGE, electroblotted to nitrocellulose and visualized with the anti-human PDGF antibody. Five nanograms of purified platelet PDGF was run as reference.

The results indicated constitutive secretion of several species of molecules which are immunologically similar to platelet PDGF but are of higher relative molecular weight (36–39 kD) than the expected 30–32 kD MW of platelet PDGF or A chain or B chain homodimers. Chemotactic and mitogenic assays performed with this serum-free conditioned media indicated the total biological activity present was equivalent to 15 ng/ml of platelet PDGF after a 48 hour conditioning period. Incubation of the media with 30 μg/ml of anti-human PDGF IgG neutralized approximately 20–30% of the mitogenic activity and similar amount of the chemotactic activity.

The presence in HUVE culture media of several species of PDGF immunoreactive molecules was unexpected, particularly molecules of higher molecular weight than those of the A and B chain dimeric molecules anticipated to be produced and secreted by endothelial cells (Collins, et al, *Nature,* 328:621–624, 1987; Sitaras, et al., *J. Cell. Physiol.,* 132:376–380, 1987). In order to obtain greater amounts of the PDGF-like proteins for further analysis, the HUVE cells had to be kept in media containing 20% fetal calf serum, since the cells begin to die after 24 hours in serum-free or low serum media. The PDGF immunoreactive proteins were partially purified from the serum containing media by use of an antibody affinity column made with the anti-human PDGF IgG and an Affi-Gel 10 support (BioRad). Mitogenic assays were performed using NRK cells as target cells (PDGF BB =5 ng/ml, PDGF AA=10 ng/ml). HUVE media was 250 μl of HUVE cell serum-free conditioned media (48 hours) which was dialyzed against 1 N acetic acid, lyophilized, and resuspended in DMEM before addition to test wells. Affinity purified fraction was 5 μl/ml of combined, concentrated major pool from Affi-Gel 10 affinity column. Anti-PDGF IgG or non-immune IgG (30 μg/ml) was added to the samples and incubated 18 hours at 4° C. prior to testing in the mitogenic assay. The mean of triplicate samples was determined and the standard deviation was less than 5%. The experiments were repeated at least three times with similar results.

When aliquots of the partially purified proteins were assayed for chemotactic and mitogenic activity, ail biological activity could be neutralized by prior incubation of the proteins with the ant-human PDGF antibody. This indicated that the only biologically active molecules present in the partially purified media proteins were PDGF immunorelated molecules.

Aliquots of the partially purified proteins were immunoblotted using the same anti-PDGF antibody and the data indicated the presence of the higher MW molecules observed in the serum-free conditioned media. The major species secreted migrates on polyacrylamide gels at 36 kD and comprises at least 50% of the total immunoreactive protein purified from conditioned media. The immunoreactive species migrating at 37 and 39 kD constitute most of the remaining immunoreactive protein. A similar pattern was seen with proteins labeled with $^{35}$S-cysteine and affinity purified with the anti-PDGF IgG immunoaffinity column. Less than 15% of the total affinity purified proteins co-migrated with purified platelet PDGF or recombinant PDGF isoforms.

Prior incubation of the antibody with purified PDGF (300 ng PDGF/2 μg IgG) blocked antibody binding to all of the molecules, indicating shared antigenic determinants with dimeric platelet PDGF. Interestingly, when the antibody was blocked with recombinant AA, BB, or AB dimers, antibody binding to the HUVE secreted proteins was inhibited equally by all three dimeric forms, suggesting that the antibody recognizes common epitopes present on all three PDGF dimers and the HUVE secreted molecules. In order to insure tat none of the antibody binding molecules detected on Western blots was derived from fetal calf serum or other additives in the culture media, a new, unused antibody affinity column was made and media which was never conditioned by cells was processed exactly as the conditioned media. No PDGF immunoreactive molecules were detected in the fractions from this column by immunoblot and no biological activity was detected. When platelet PDGF or the recombinant dimers are reduced with 200 mM dithiothreitol (DTT), monomeric A chain (17 kD) and 8 chain (14 kD) peptides are observed on immunoblots. Treating the HUVE molecules in a 100 mM OTT sample buffer resulted in slower migration of the major immunoreactive peptides on polyacrylamide gels. Most of the immunoreactive molecules migrated at 38–39 kD and less intense bands were observed at 25 and 14 kD. It was necessary to run at least 10 times as much reduced protein as nonreduced in order to detect the reduced molecules. This is consistent with the affinity of the antibody for monomeric forms of the PDGF A and B chain peptides. These data indicate that the major species in the PDGF-related affinity purified proteins from conditioned media of HUVE cells was monomeric peptide which migrates on acrylamide gels at an apparent molecular weight of 36 kD nonreduced and 38 kD when reduced.

EXAMPLE 2

Biological Assays

Chemotactic activity was determined in the Boyden chamber chemotaxis assay with NIH 3T3 or bovine aortic smooth muscle (BASM) cells as described (Grotendorst, et al., *Proc. Natl. Acad. Sci. USA,* 78:3669–3672, 1981; Grotendorst, et al., *Methods in Enzymol.,* 147:1 44152, 1987). Mitogenic assays were performed using 96 well plates and normal rat kidney (NRK) fibroblasts or NIH 3T3 cells as target cells. The cells were plated in DMEM, 10% FCS; NRK cell cultures were used 10–14 days after confluence and 3T3 cells made quiescent by incubation for 2 days in serum-free DMEM, 0.2 mg/ml BSA before use. Sample proteins and dilutions of known standards were added to the wells and the plates incubated at 37° C. in 10% $CO_2$, 90% air for 18 hours, after which $^3$H-thymidine at a final concentration of 5 uCi/ml was added and incubated for an additional 2 hours. The media was removed, the cells washed and DNA synthesis determined from the $^3$H-thymidine incorporation into trichloroacetic acid precipitable material by scintillation counting.

Gel Electrophoresis and Immunoblotting

Electrophoresis was performed on 12% polyacrylamide gels containing SDS (Laemmli, U.K., *Nature,* 227:680–685, 1970) unless otherwise stated. Immunoblotting was performed by electroblotting the proteins to a nitrocellulose membrane and incubating the membrane in 50 mM Tris-HCl, pH 7.4, 100 mM NaCl (TBS) with 5% non-fat dry milk at 25° C. for 1 hour to block non-specific antibody binding.

The blocking solution was removed and the antibody (15 μg/ml) added in TBS containing 0.5% non-fat dry milk and 1 μg/ml sodium azide and incubated overnight at 25° C. The membranes were washed 5 times in TBS, 0.5% milk for 10 minutes each wash and then incubated with alkaline phosphatase conjugated affinity purified rabbit anti-goat IgG (KPL, Gaithersburg, Md.) at a 1:1000 dilution in TBS containing 0.5% milk at 25° C. for 1 hour. The filters were washed with TBS five times, 10 minutes each time, and the blot developed using an alkaline phosphatase substrate solution (0.1 M Tris-HCl, pH 9, 025 mg/ml nitro blue tetrazolium, 0.5 mg/ml 5 bromo-4-chloro-3-indolyl phosphate).

Major Chemotactic and Mitogenic Activity is Produced by 36 kD Peptide and Not PDGF Peptides In order to determine if the chemotactic and mitogenic activities observed in the partially purified media proteins were from molecules containing the PDGF A and B chain peptides or were the products of molecules which do not contain these sequences, biological assays were performed with serial dilutions of the affinity purified media proteins and serial dilutions of recombinant PDGF AA and BB homodimers and the AB heterodimer. Sufficient quantities of the samples were prepared to perform the mitogenic and chemotactic assays and the immunoblots with aliquots of each dilution sample. The mitogenic activity of the HUVE affinity purified factors observed was comparable to the activity elicited by all three recombinant PDGF dimers. The chemotactic activity was comparable to the AB heterodimer, producing less response than the BB homodimer and greater response than the AA homodimer. When the biological activity of the samples was compared with immunoblots of equivalent amounts of the same samples, no A chain nor B chain molecules were detected in the test samples. These data demonstrate the major biological activity present in the anti-PDGF affinity purified fraction cannot be accounted for by PDGF A or B chain containing molecules and imply that the major PDGF-immunoreactive protein species present in these samples (the 36 kD peptide) is biologically active and does not contain amino acid sequences found in the amino and carboxy terminals of the PDGF A or B chain peptides.

EXAMPLE 3

Receptor Competition Assays

Assays were performed using confluent cultures of NIH 3T3 cells in 24 well plates (Costar) grown in DMEM, 10% fetal calf serum, 10 μg/ml Gentamicin. The growth media was removed and the cells washed twice with serum-free DMEM, 0.2 mg/ml BSA and the plates placed on ice for 30 minutes in serum-free DMEM, 0.2 mg/ml BSA. Test samples and controls were made up in serum-free DMEM, 0.2 mg/ml BSA containing 5–10 ng/ml of HUVE affinity purified proteins and a serial dilution of one of the recombinant PDGF isoforms in a concentration range of 300 ng/ml to 16 ng/ml. One milliliter aliquots of the samples were placed into wells of the 24 well plates and incubated on ice on a platform rocker for two hours. After the incubation period, the cells were washed three times for 10 minutes each on ice with PBS. The proteins bound to the surface of the cells were eluted with 5 ul of 1 N acetic acid for 10 minutes. The acetic acid elution samples were lyophilized, resuspended in 5 mM HCl, run on 12% polyacrylamide gels and immunoblotted to nitrocellulose using the ant-PDGF antibody.

In order to substantiate the binding of the endothelial cell molecules to the PDGF cell surface receptors, competitive receptor binding assays were performed. Because immunoblots of the affinity purified HUVE cell secreted proteins indicated the presence of multiple PDGF immunoreactive molecules, $^{125}$I-labeled PDGF competition assays could not be used since this would not indicate which molecules in this mixture were competing for binding of the labeled PDGF for the receptors an the target cells. Since the isoforms of PDGF and the major PDGF immunorelated protein secreted by HUVE cells are of different molecular weights, receptor binding competition was demonstrated on immunoblots. Direct binding of the anti-PDGF immunoreactive peptides to NIH 3T3 cells was demonstrated by incubating monolayers of the 3T3 fibroblasts with the anti-PDGF affinity purified proteins (10 ng/ml) for 2 hours at 4° C. Bound peptides were released by washing of the cell layer with 1 N acetic acid and quantitated by immunoblot analysis using anti-PDGF IgG. This data show that the 36 kD immunoreactive peptide binds to cell surface of NIH 3T3 cells. This binding can be competed by increasing concentrations of recombinant PDGF BB added to the binding media. These data suggest that the CTGF peptide binds to specific cell surface receptors on NIH 3T3 cells and that PDGF BB can compete with this binding.

RNA Isolation and Northern Blotting

Total RNA was isolated from cells in monolayer culture cells. Lyophilized RNA was resuspended in gel loading buffer containing 50% formamide and heated at 95° C. for two minutes before loading (20 μg per lane total RNA) onto 2.2 M formaldehyde, 1 % agarose gels and run at 50 volts. Integrity of RNA was determined by ethidium bromide staining and visualization of 18S and 28S rRNA bands. After electrophoresis the RNA was transferred to nitrocellulose by blotting overnight with 10× SSC buffer. The nitrocellulose was air dried and baked at 80° C. for 2 hours in a vacuum oven. Hybridization was performed overnight at 46° C. with the addition of 5×10$^5$ CPM per ml of $^{32}$P-labeled probe. Normally for Northern blots, the entire plasmid was labeled and used as a probe. Labeling was done with a random primer labeling kit from Boehringer Mannheim. After hybridization, membranes were washed twice in 2× SSC, 0.1% SDS for 15 minutes each at room temperature, once for 15 minutes in 0.1× SSC, 0.1% SDS, room temperature and a final 15 minutes wash in 0.1× SSC, 0.1% SDS at 46° C. Blots were autoradiographed at −70° C. on Kodak X-omat film.

EXAMPLE 4

Library Screening, Cloning, and Sequencing

Standard molecular biology techniques were used to subclone and purify the various DNA clones (Sambrook, et al., *Molecular Cloning a Laboratory Manual*, Second edition, Cold Spring Harbor Laboratory Press, Col. Spring Harbor, N.Y). Clone DB60 was picked from a lambda gt11 HUVE cell cDNA library by induction of the fusion proteins and screening with anti-PDGF antibody. Plaques picked were rescreened and positive clones replated at low titer and isolated.

The EcoR I insert from clone DB60 was cloned into the M13 phage vector and single-stranded DNA obtained for clones with the insert in opposite orientations. These M13 clones were then sequenced by the dideoxy method using the Sequenase kit (U.S. Biochemical) and $^{35}$S-dATP (duPont). Both strands of DNA for this clone were completely sequenced using primer extension and both GTP and ITP chemistry. Aliquots of the sequencing reactions were run on both 6% acrylamide (16 hours) and 8% acrylamide (6 hours) gels, vacuum dried and autoradiographed for at least 18 hours.

The cDNA fragment from clone DB60 was $^{32}$P-CTP labeled and used to rescreen the HUVE cell cDNA lambda gt11 library. Several clones were picked and the largest, the 2100 bp clone designed DB60R32, was subcloned into Bluescript phagemid. Subclones were made of Pst I, Kpn 1, and Eco RI/Kpn I restriction fragments also in Bluescript These subclones were sequenced by double-stranded plasmid DNA sequencing techniques using Sequenase as described above. The 1458 bp Eco RI/Kpn I clone containing the open reading frame was subcloned into M13 mp18 and M 13 mp19 and both strands of DNA were completely sequenced using single-stranded DNA sequencing techniques with primer extension and both GTP and ITP chemistry.

Cloning Expression and Sequencing of the cDNA for Connective Tissue Growth Factor In order to further characterize these PDGF related molecules, sufficient quantities of the CTGF protein for amino acid sequencing was needed. However, the low concentrations of CTGF in the conditioned media of HUVE cell cultures and the costly and time consuming techniques involved in obtaining and culturing these cells made protein purification to homogeneity and amino acid sequencing impractical. Therefore, the anti-PDGF antibody was used to screen an HUVE cell cDNA library made in the expression vector lambda gt11. Over 500,000 recombinant clones were screened. Several clones which gave strong signals with the anti-PDGF antibody in the screening process were purified and subcloned into the Ml 3 phage vector and partial sequence data obtained by single-stranded DNA sequencing. A search of the GenBank DNA sequence data base indicated that two of the clones picked contained fragments of the PDGF B chain cDNA open reading frame sequence. One of these clones was similar to a 1.8 kb insert previously isolated by Collins, et al. (*Nature*, 316:748–750, 1985) using a c-sis cDNA probe. A third clone of 500 bp was completely sequenced and no match was found in a homology search of all nucleotide and amino acid sequences in GenBank (CEF 10 sequence was not available at that time). This clone was designated DB60. Anti-PDGF antibody binding to the fusion protein produced by the clone DB60 was completely blocked by the affinity purified proteins. A $^{32}$P-labeled probe was made of DB60 and used on a Northern blot of 20 μg of total RNA isolated from HUVE cells. The blot indicated probe hybridization with an mRNA of 2.4 kilobases, which is a message of sufficient size to produce the proteins in the 38 kD molecular weight range seen on the immunoblots of the affinity purified proteins. The DB60 clone was used to rescreen the HUVE cell cDNA lambda gt11 library and the largest clone isolated contained a 2100 base pair insert designated DB60R32. A probe made with the 2100 bp Eco RI insert of clone DB60R32 also hybridized with a single 2.4 kb message in a Northern blot of total RNA from HUVE cells.

EXAMPLE 5

In Vitro Transcription and Translation

In vitro transcription reactions were done using the 2100 bp cDNA clone DB60R32 in the Bluescript KS vector. The plasmid was cut with Xho I which cuts the plasmid once in the multiple cloning site of the vector 3' to the cDNA insert. The T7 promoter site located 5' to the cDNA insert was used for transcription. The in vitro transcriptions were done with a kit supplied with the Bluescript vector (Stratagene).

In vitro translation reactions were done using nuclease treated rabbit reticulocyte lysate and $^{35}$S-cysteine in a cysteine-free amino acid mix for labeling of the peptide (Promega). The reactions were done in a final volume of 50 ul containing $^{35}$S-cysteine 1 mCi/ml (1200 Ci/mMole, DuPont), and serial dilutions of mRNA from the in vitro transcription reactions in concentrations ranging from 50 to 500 nanograms per reaction tube. The reactions were incubated at 30° C. for 60 minutes. Aliquots of the reactions were run on reduced or nonreduced 12% polyacrylamide electrophoresis gels, dried, and autoradiographed.

Bacterial expression of immunoreactive CTGF peptide was accomplished by subcloning clone DB60R32 into the Eco RI site of the pET 5 expression vector (Studier, et al., *Ed. Academic Press*, N.Y. Vol. 185, 60–89, 1990) in both sense and inverse orientations (as determined by restriction enzyme digest analysis). Cultures of *E. coli* HMS174 cells were grown in M9 media to an OD 600 of 0.7 and the media made 0.4 mM IPTG and incubation continued for 2 hours. The cells were pelleted, lysed, inclusion bodies removed by centrifugation and aliquots of the pellet extracts run on 12% polyacrylamide gels and immunoblotted using the anti-PDGF antibody. The protein produced by clone DB60R32 in the sense orientation produced anti-PDGF immunoreactive peptides in the 36–39 kD MW range while the anti-sense control produced no immunoreactive peptides. The recombinant peptdies produced in the *E. Coli* system completely blocked the anti-PDGF reaction with the CTGF peptides present in conditioned media.

Expression of CTGF in Xenopus

For expression in *Xenopus oocytes*, mature *X. laevis* females were obtained from Nasco (Fort Atkinson, Wis.) and maintained at room temperature. Frogs were anesthetized by hypothermia and the ovarian tissue was surgically removed. Ovarian tissue was minced and digested the 0.2% collagenase (Sigma Type II) in OR-2 without calcium (Wallace, et al, *Exp. Zool.*, 184:321–334, 1973) for 2–3 hours. Unblemished stage VI oocytes (Dumont, *J. Morphol.*, 136:153–180, 1972), 1.3 mm diameter, were then carefully selected and microinjected.

Stage VI oocytes (5–10 at a time) were placed on a hollowed plexiglass platform and drained of excess OR-2 solution. Approximately 50 nl of sample containing 10 ng of RNA was injected into the animal pole just above the oocyte equator using a Leitz system microinjector. Following injection, oocytes were returned to OR-2 buffer with 0.1% BSA and incubated for 24 hours at 25° C. Viable oocytes were then pooled and extracted by homogenization in 100 mm NaCl, 10 mm Tris pH 7.5 with ten strokes of a Dounce homogenizer (20 µl/oocyte). The homogenate was then mixed with an equal volume of freon to remove pigment and lipid and centrifuged at 10,000 rpm for 30 seconds to separate the phases. The top aqueous phase was removed and tested for chemotactic activity using NIH 3T3 cells as described above.

Injection of Xenopus oocytes with 10 ng of RNA preparations derived by in in vitro transcription of the DB60 R32 clone resulted in the production of a fibroblast chemotactic activity. Control injected cells did not produce this activity. These results indicate that the open reading frame of the DB60 R32 done encodes a protein with chemotactic activity for fibroblastic cells as does CTGF.

EXAMPLE 6

Sequence Analysis of CTGF

The 2100 bp insert of clone DB60R32 was sequenced initially by subcloning of Pst I and Kpn I restriction fragments into Bluescript and using double-stranded dideoxy methods. This indicated an open reading frame of 1047 base pairs and oriented the DB60 insert to the larger cDNA. An Eco RI/Kpn I fragment containing the entire open reading frame was inserted into Ml 3 mp18 and M13 mp19 and both strands of the DNA were sequenced with single-stranded dideoxy methods by primer extension using both GTP and the GTP analog ITP. The cDNA nucleotide sequence of the open reading frame encoded a 38,000 MW protein, confirming the cell-free translation results and matching the size of the immunopurified peptides. A new search of the GenBank data base revealed that this cDNA had a 50% nucleotide sequence homology with CEF-10 mRNA, one of the immediate early genes induced in v-src transformed chicken embryo fibroblasts (Simmons. et al., *Proc. Natl. Acad. Sci. USA*, 86:1178–1182, 1989). The translated cDNA for human CTGF and avian CEF-10 have a 45% overall homology and a 52% homology if the putative alternative splicing region is deleted. This region is between amino acids 171 (aspartic acid) and 199 (cysteine) in the CTGF sequence.

Although the invention has been described with reference to the presently preferred embodiment it should be understood that various modifications can be made without departing from the spirit of the invention. Accordingly, the invention is limited only by the following claims.

SUMMARY OF SEQUENCES

Sequence ID No. 1 is the nucleic acid sequence (and the deduced amino acid sequence) of cDNA encoding CTGF of the present invention.

Sequence ID No. 2 is the deduced amino acid sequence of CTGF of the present invention.

What is claimed is:

1. A method for accelerating wound healing in a subject comprising contacting the site of the wound with a composition comprising an effective amount of purified connective tissue growth factor (CTGF) and an effective amount of transforming growth factor beta, which stimulates the production of CTGF in vivo.

2. A method of stimulating growth of connective tissues cells, comprising contacting the cells with an effective amount of connective tissue growth factor or active fragment thereof, thereby stimulating growth of the connective tissue cells.

3. The method of claim 2, wherein the connective tissue cells are endothelial cells.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 2075 base pairs
      (B) TYPE: nucleic acid
      (C) STRANDEDNESS: single
      (D) TOPOLOGY: linear

```
        (ii) MOLECULE TYPE: cDNA (vii) IMMEDIATE SOURCE:
            (B) CLONE: DB60R32

(ix) FEATURE:
            (A) NAME/KEY: CDS
            (B) LOCATION: 130..1177

(xi) SEQUENCE DESCRIPTION: SEQ ID NO:1:

CCCGGCCGAC AGCCCCGAGA CGACAGCCCG GCGCGTCCCG GTCCCCACCT CCGACCACCG        60

CCAGCGCTCC AGGCCCCGCG CTCCCCGCTC GCCGCCACCG CGCCCTCCGC TCCGCCCGCA       120

GTGCCAACC ATG ACC GCC GCC AGT ATG GGC CCC GTC CGC GTC GCC TTC          168
           Met Thr Ala Ala Ser Met Gly Pro Val Arg Val Ala Phe
             1               5                  10

GTG GTC CTC CTC GCC CTC TGC AGC CGG CCG GCC GTC GGC CAG AAC TGC        216
Val Val Leu Leu Ala Leu Cys Ser Arg Pro Ala Val Gly Gln Asn Cys
 15                  20                  25

AGC GGG CCG TGC CGG TGC CCG GAC GAG CCG GCG CCG CGC TGC CCG GCG        264
Ser Gly Pro Cys Arg Cys Pro Asp Glu Pro Ala Pro Arg Cys Pro Ala
 30                  35                  40                  45

GGC GTG AGC CTC GTG CTG GAC GGC TGC GGC TGC TGC CGC GTC TGC GCC        312
Gly Val Ser Leu Val Leu Asp Gly Cys Gly Cys Cys Arg Val Cys Ala
                 50                  55                  60

AAG CAG CTG GGC GAG CTG TGC ACC GAG CGC GAC CCC TGC GAC CCG CAC        360
Lys Gln Leu Gly Glu Leu Cys Thr Glu Arg Asp Pro Cys Asp Pro His
             65                  70                  75

AAG GGC CTC TTC TGT GAC TTC GGC TCC CCG GCC AAC CGC AAG ATC GGC        408
Lys Gly Leu Phe Cys Asp Phe Gly Ser Pro Ala Asn Arg Lys Ile Gly
         80                  85                  90

GTG TGC ACC GCC AAA GAT GGT GCT CCC TGC ATC TTC GGT GGT ACG GTG        456
Val Cys Thr Ala Lys Asp Gly Ala Pro Cys Ile Phe Gly Gly Thr Val
 95                 100                 105

TAC CGC AGC GGA GAG TCC TTC CAG AGC AGC TGC AAG TAC CAG TGC ACG        504
Tyr Arg Ser Gly Glu Ser Phe Gln Ser Ser Cys Lys Tyr Gln Cys Thr
110                 115                 120                 125

TGC CTG GAC GGG GCG GTG GGC TGC ATG CCC CTG TGC AGC ATG GAC GTT        552
Cys Leu Asp Gly Ala Val Gly Cys Met Pro Leu Cys Ser Met Asp Val
                130                 135                 140

CGT CTG CCC AGC CCT GAC TGC CCC TTC CCG AGG AGG GTC AAG CTG CCC        600
Arg Leu Pro Ser Pro Asp Cys Pro Phe Pro Arg Arg Val Lys Leu Pro
            145                 150                 155

GGG AAA TGC TGC GAG GAG TGG GTG TGT GAC GAG CCC AAG GAC CAA ACC        648
Gly Lys Cys Cys Glu Glu Trp Val Cys Asp Glu Pro Lys Asp Gln Thr
        160                 165                 170

GTG GTT GGG CCT GCC CTC GCG GCT TAC CGA CTG GAA GAC ACG TTT GGC        696
Val Val Gly Pro Ala Leu Ala Ala Tyr Arg Leu Glu Asp Thr Phe Gly
175                 180                 185

CCA GAC CCA ACT ATG ATT AGA GCC AAC TGC CTG GTC CAG ACC ACA GAG        744
Pro Asp Pro Thr Met Ile Arg Ala Asn Cys Leu Val Gln Thr Thr Glu
190                 195                 200                 205

TGG AGC GCC TGT TCC AAG ACC TGT GGG ATG GGC ATC TCC ACC CGG GTT        792
Trp Ser Ala Cys Ser Lys Thr Cys Gly Met Gly Ile Ser Thr Arg Val
                210                 215                 220

ACC AAT GAC AAC GCC TCC TGC AGG CTA GAG AAG CAG AGC CGC CTG TGC        840
Thr Asn Asp Asn Ala Ser Cys Arg Leu Glu Lys Gln Ser Arg Leu Cys
            225                 230                 235

ATG GTC AGG CCT TGC GAA GCT GAC CTG GAA GAG AAC ATT AAG AAG GGC        888
Met Val Arg Pro Cys Glu Ala Asp Leu Glu Glu Asn Ile Lys Lys Gly
        240                 245                 250
```

```
AAA AAG TGC ATC CGT ACT CCC AAA ATC TCC AAG CCT ATC AAG TTT GAG        936
Lys Lys Cys Ile Arg Thr Pro Lys Ile Ser Lys Pro Ile Lys Phe Glu
        255                 260                 265

CTT TCT GGC TGC ACC AGC ATG AAG ACA TAC CGA GCT AAA TTC TGT GGA        984
Leu Ser Gly Cys Thr Ser Met Lys Thr Tyr Arg Ala Lys Phe Cys Gly
270                 275                 280                 285

GTA TGT ACC GAC GGC CGA TGC TGC ACC CCC CAC AGA ACC ACC ACC CTG       1032
Val Cys Thr Asp Gly Arg Cys Cys Thr Pro His Arg Thr Thr Thr Leu
                290                 295                 300

CCG GTG GAG TTC AAG TGC CCT GAC GGC GAG GTC ATG AAG AAG AAC ATG       1080
Pro Val Glu Phe Lys Cys Pro Asp Gly Glu Val Met Lys Lys Asn Met
        305                 310                 315

ATG TTC ATC AAG ACC TGT GCC TGC CAT TAC AAC TGT CCC GGA GAC AAT       1128
Met Phe Ile Lys Thr Cys Ala Cys His Tyr Asn Cys Pro Gly Asp Asn
                320                 325                 330

GAC ATC TTT GAA TCG CTG TAC TAC AGG AAG ATG TAC GGA GAC ATG GCA T     1177
Asp Ile Phe Glu Ser Leu Tyr Tyr Arg Lys Met Tyr Gly Asp Met Ala
        335                 340                 345

GAAGCCAGAG AGTGAGAGAC ATTAACTCAT TAGACTGGAA CTTGAACTGA TTCACATCTC     1237

ATTTTTCCGT AAAAATGATT TCAGTAGCAC AAGTTATTTA AATCTGTTTT TCTAACTGGG     1297

GGAAAAGATT CCCACCCAAT TCAAAACATT GTGCCATGTC AAACAAATAG TCTATCTTCC     1357

CCAGACACTG GTTTGAAGAA TGTTAAGACT TGACAGTGGA ACTACATTAG TACACAGCAC     1417

CAGAATGTAT ATTAAGGTGT GGCTTTAGGA GCAGTGGGAG GGTACCGGCC CGGTTAGTAT     1477

CATCAGATCG ACTCTTATAC GAGTAATATG CCTGCTATTT GAAGTGTAAT TGAGAAGGAA     1537

AATTTTAGCG TGCTCACTGA CCTGCCTGTA GCCCCAGTGA CAGCTAGGAT GTGCATTCTC     1597

CAGCCATCAA GAGACTGAGT CAAGTTGTTC CTTAAGTCAG AACAGCAGAC TCAGCTCTGA     1657

CATTCTGATT CGAATGACAC TGTTCAGGAA TCGGAATCCT GTCGATTAGA CTGGACAGCT     1717

TGTGGCAAGT GAATTTGCCT GTAACAAGCC AGATTTTTTA AAATTTATAT TGTAAATATT     1777

GTGTGTGTGT GTGTGTGTGT ATATATATAT ATATATGTAC AGTTATCTAA GTTAATTTAA     1837

AGTTGTTTGT GCCTTTTTAT TTTTGTTTTT AATGCTTTGA TATTTCAATG TTAGCCTCAA     1897

TTTCTGAACA CCATAGGTAG AATGTAAAGC TTGTCTGATC GTTCAAAGCA TGAAATGGAT     1957

ACTTATATGG AAATTCTGCT CAGATAGAAT GACAGTCCGT CAAAACAGAT TGTTTGCAAA     2017

GGGGAGGCAT CAGTGTCTTG GCAGGCTGAT TTCTAGGTAG GAAATGTGGT AGCTCACG      2075

(2) INFORMATION FOR SEQ ID NO:2:

(i) SEQUENCE CHARACTERISTICS:
        (A) LENGTH: 349 amino acids
        (B) TYPE: amino acid
        (D) TOPOLOGY: linear (ii) MOLECULE TYPE: protein (xi) SEQUENCE DESCRIPTION: SEQ ID NO:2:

Met Thr Ala Ala Ser Met Gly Pro Val Arg Val Ala Phe Val Val Leu
  1               5                  10                  15

Leu Ala Leu Cys Ser Arg Pro Ala Val Gly Gln Asn Cys Ser Gly Pro
                 20                  25                  30

Cys Arg Cys Pro Asp Glu Pro Ala Pro Arg Cys Pro Ala Gly Val Ser
             35                  40                  45

Leu Val Leu Asp Gly Cys Gly Cys Cys Arg Val Cys Ala Lys Gln Leu
 50                  55                  60
```

-continued

```
Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
                100                 105                 110

Gly Glu Ser Phe Gln Ser Ser Cys Lys Tyr Gln Cys Thr Cys Leu Asp
                115                 120                 125

Gly Ala Val Gly Cys Met Pro Leu Cys Ser Met Asp Val Arg Leu Pro
            130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
                180                 185                 190

Thr Met Ile Arg Ala Asn Cys Leu Val Gln Thr Thr Glu Trp Ser Ala
                195                 200                 205

Cys Ser Lys Thr Cys Gly Met Gly Ile Ser Thr Arg Val Thr Asn Asp
        210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
                260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
        290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
                340                 345
```